United States Patent [19]

Lasner et al.

[11] Patent Number: 4,527,331
[45] Date of Patent: Jul. 9, 1985

[54] SUTURE REMOVER AND CONTINUOUS BAND SCISSORS

[76] Inventors: Jeffrey I. Lasner, 4 Baltusrol Dr., Purchase, N.Y. 10577; Francisco H. Aleixo, 66 John St., Tarrytown, N.Y. 10591

[21] Appl. No.: 465,873

[22] Filed: Feb. 11, 1983

Related U.S. Application Data

[63] Continuation-in-part of Ser. No. 342,765, Jan. 26, 1982, abandoned.

[51] Int. Cl.³ .................................................. B26B 13/16
[52] U.S. Cl. ........................................ 30/135; 30/234; 30/261
[58] Field of Search ............... 30/134, 234, 261, 135, 30/254, 266, 235

[56] References Cited

U.S. PATENT DOCUMENTS

| | | | |
|---|---|---|---|
| 590,330 | 9/1897 | Nolen | 30/254 |
| 842,292 | 1/1907 | Allen | 30/234 |
| 1,637,607 | 8/1927 | Eggers | 30/234 |
| 2,865,099 | 12/1958 | Blackwood | 30/134 |
| 3,003,236 | 10/1961 | Castelli | 30/234 X |
| 3,325,897 | 6/1967 | Luebkeman | 30/254 |
| 3,443,313 | 5/1969 | Profy | 30/134 |
| 3,659,343 | 5/1972 | Straus | 30/124 |
| 4,133,107 | 1/1979 | Vogel | 30/266 |
| 4,246,698 | 1/1981 | Lasner et al. | 30/134 |
| 4,268,962 | 5/1981 | Doiron | 30/261 |

FOREIGN PATENT DOCUMENTS 774767 5/1957 United Kingdom ............... 30/254

*Primary Examiner*—Jimmy C. Peters
*Attorney, Agent, or Firm*—Alfred E. Miller

[57] ABSTRACT

An improved surgical suture remover is formed of a single elongated strip of resiliently flexible material having a bend substantially midway in its elongation to define first and second shanks respectively carrying a blade and a shearing portion at their corresponding ends. The blade includes a cutting section, and the shearing portion includes a cutting edge, and the blade and shearing portion are pivotally connected for movement of the cutting section and cutting edge toward and away from each other along a cutting plane to cooperatively sever a suture therebetween. An elongated suture gripping element unitarily depending from the shearing portion includes a contact area for suture gripping contact with the cutting section during an operating stroke or jaw closure of the instrument. In another embodiment there is a cutting blade and a shear blade forming a scissors, with each blade having an elongated raised rib, and an abutment shoulder. The ribs render the blade tips inflexible and bow the blades relative to each other, in order to provide edge-to-edge contact between the blades.

14 Claims, 11 Drawing Figures

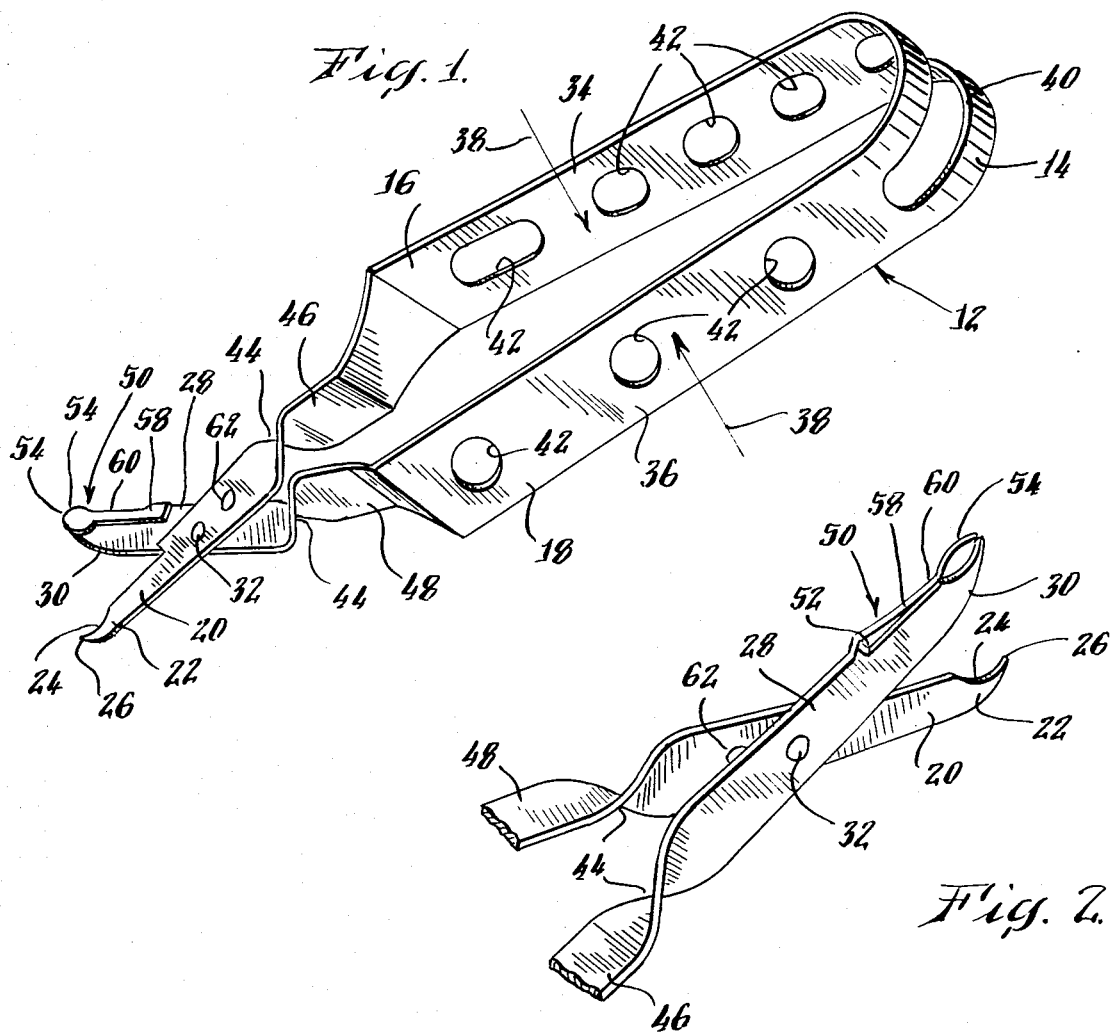
Fig. 1.
Fig. 2.
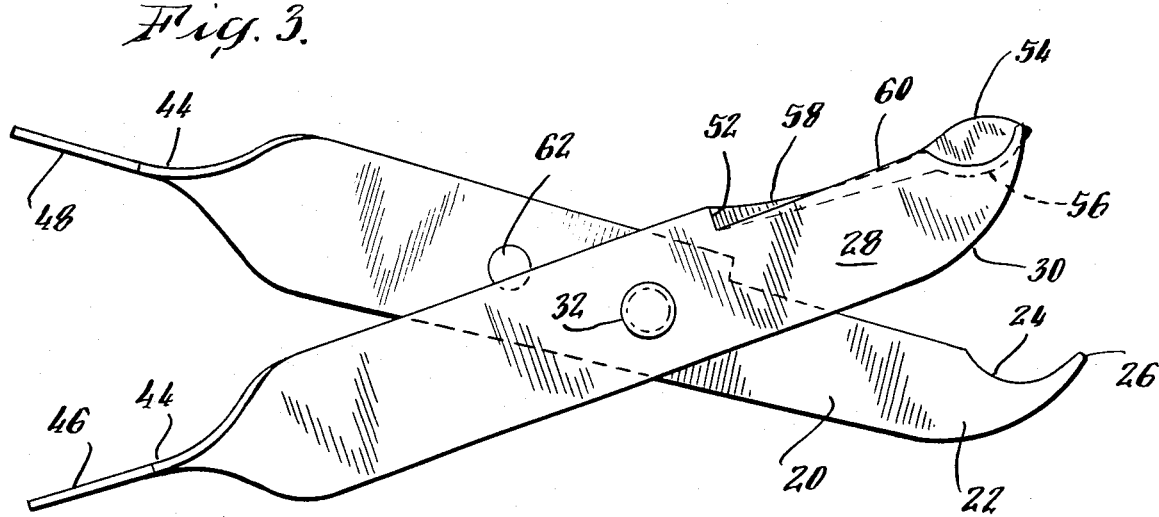
Fig. 3.

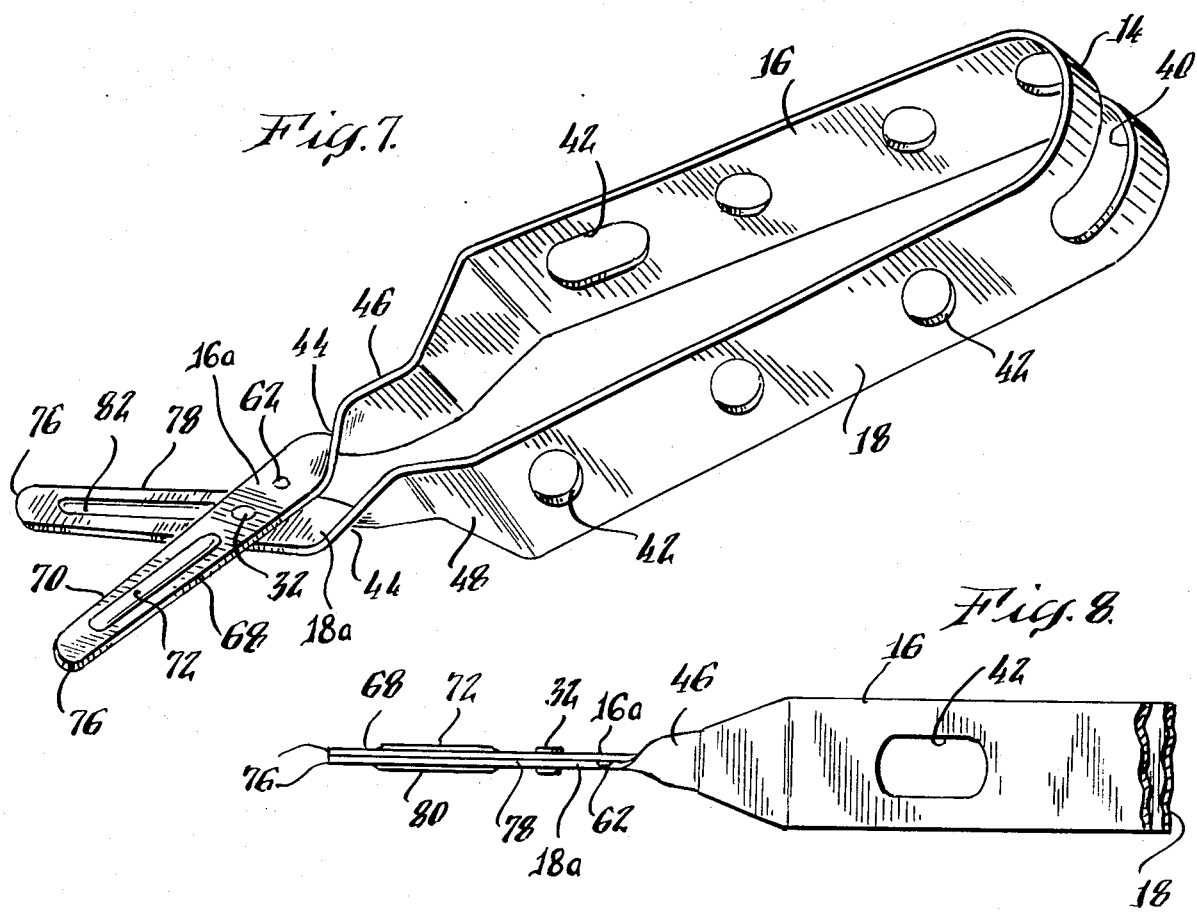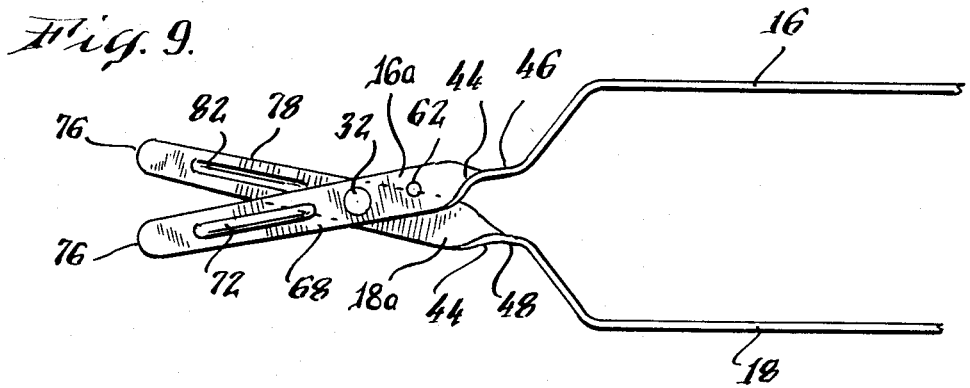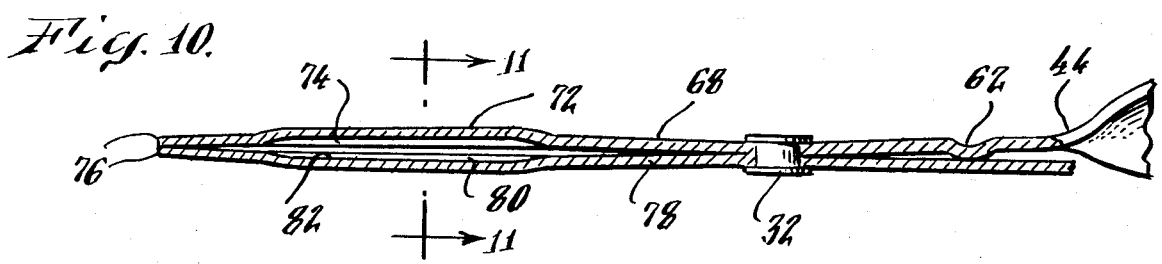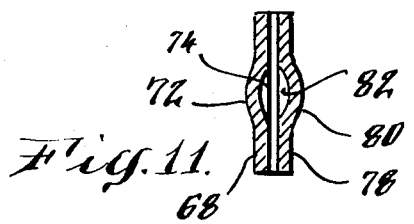

SUTURE REMOVER AND CONTINUOUS BAND SCISSORS

This invention is a continuation-in-part of our co-pending application Ser. No. 342,765, filed on Jan. 26, 1982 now abandoned.

FIELD OF THE INVENTION

The present invention relates to an improved surgical suture remover and, more particularly, to such an instrument that is capable of both cutting and gripping a suture so that a surgeon can, with one hand, cut the stitches and withdraw the cut thread, and that is readily manufacturable at relatively low cost with a high degree of precision and reliability.

BACKGROUND OF THE INVENTION

In U.S. Pat. No. 4,246,698 of Jan. 17, 1981—the disclosure of which is expressly incorporated by reference herein—the present inventors teach a suture remover surgical instrument of generally scissor-like configuration in which a pair of shanks are pivotally connected intermediate their ends for relative movement therebetween. The first shank carries on one of its ends a blade having a cutting section, while the second shank carries on its corresponding end a shearing portion having a cutting edge, so that the cutting section and cutting edge are movable toward and away from each other along a cutting plane. An elongated suture gripping element formed of a resilient material includes a contact area at one end and is attached as by soldering, at its other end to the shearing portion, the contact area being so disposed that as the cutting section and cutting edge are operatively moved toward each other along the cutting plane for shearing contact with a suture, the gripping element is deformed whereby its contact portion is resiliently moved along the cutting plane and substantially perpendicular to its elongation. In addition, a bend provided in and along the place of the gripping element adjacent its end connection to the shearing portion advantageously facilitates distribution of the deformation of the gripping element between the bend and the end connection to prevent premature deterioration of the end connection and thereby extend the useful operational life of the instrument.

The present invention represents an improvement over applicants' prior teaching. A particularly advantageous feature of the instant invention lies in its construction from a single, elongated strip of material so that each of the structural elements of the suture remover instrument—including the gripping element—are unitarily formed and integrally connected. In addition to substantially reducing the number of manufacturing steps and, therefore, its production cost, the entirely unitary, one-piece construction of the instrument essentially eliminates the possibility of premature deterioration or breakage of soldered or otherwise bonded or separately connected elements and thereby provides notably increased reliability in a precision suture removing instrument. Moreover, the modified tweezer-like configuration and various structural features of the preferred embodiment herein disclosed provide improved operating characteristics and attributes over functionally similar prior art devices with increased reliability and at reduced production cost.

It is accordingly the desideratum of the present invention to provide an improved suture remover for cutting and gripping a surgical suture, in which the instrument is formed of a single, elongated strip of material so that all of its structural elements are unitarily integral and its operating reliability correspondingly increased.

It is a particular object of the invention to provide such a suture remover that is readily manufacturable utilizing well known techniques at substantially reduced cost over similar prior art devices without decreasing its utility or sacrificing its features or abilities with respect thereto.

It is a further object of the invention to provide such a suture remover constructed of a resiliently deformable material in a modified tweezer-like configuration such that only a minimum operating force need be applied by a user to cut and grip a surgical suture.

Other objects and features of the present invention will become apparent from the following detailed description of a preferred embodiment considered in connection with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein similar reference characters denote similar elements throughout the several views:

FIG. 1 is a perspective view taken from below of an improved surgical suture remover constructed in accordance with the teachings of the present invention;

FIG. 2 is an enlarged elevated perspective view of the forward or suture cutting and gripping portion of the suture remover of FIG. 1 taken from the top rear with respect to FIG. 1;

FIG. 3 is a rear face view with respect to FIG. 1 of the forward portion of the suture remover of the invention;

FIG. 7 is a perspective view taken from above of a scissors or a cutting implement, constructed in accordance with the teachings of the present invention;

FIG. 8 is a partial side elevational of the scissors construction shown in FIG. 7;

FIG. 9 is a partial top plan view of the scissors shown in FIG. 7;

FIG. 10 is an enlarged cross sectional view of a part of said scissors shown in FIG. 7, and FIG. 11 is a cross sectional view taken along the lines of 11—11 of FIG. 10.

DETAILED DESCRIPTION OF THE PREFERRED EMBODIMENT

Figure 4:
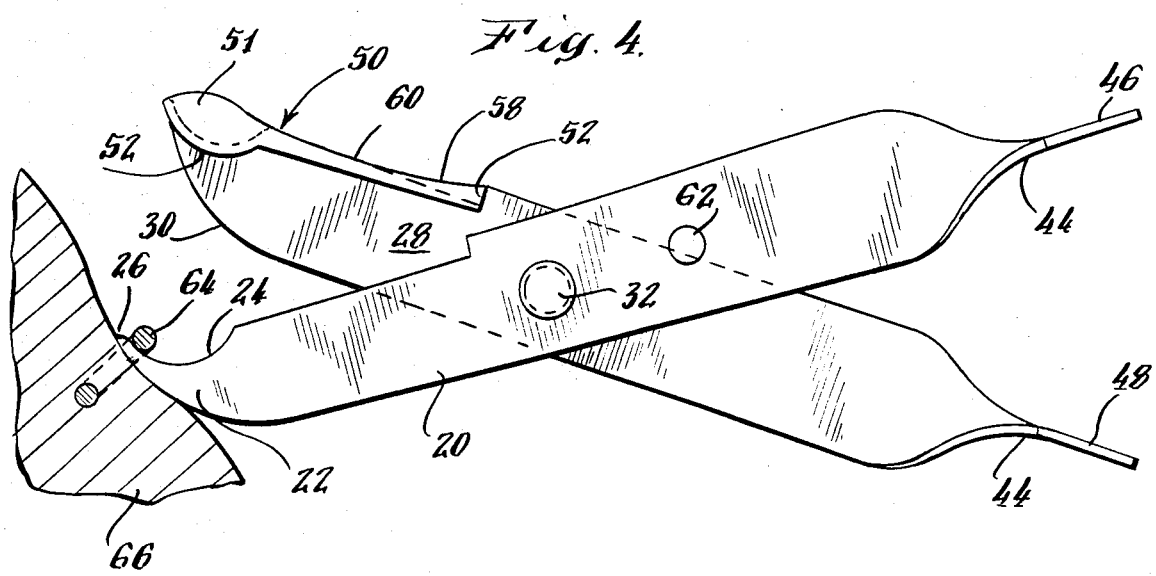
FIG. 4 is a front face view of the forward portion of the suture remover in accordance with the invention illustrating the instrument in its normal, jaws open condition at the start of a suture cutting and gripping operation.

A preferred embodiment of an improved suture remover instrument in accordance with the invention, designated by the general reference numeral 10, is shown in FIG. 1. The surgical instrument 10 is formed of a single, initially elongated strip 12 of a resiliently flexible and deformable material such as—by way of example only—stainless steel. Strip 12 is provided with a gradual, arcuate central bend 14 substantially midway in its elongation to define a first shank 16 and a second shank 18 disposed in substantially spaced apart relation.

First shank 16 unitarily carries, on its end remote from central bend 14, an integral blade 20 which includes a cutting section 22 proximate its free end. In the preferred embodiment herein disclosed, cutting section 22 is provided with an arcuately concave surface or portion 24 and terminates in an end or tip 26 that is preferably somewhat rounded or smoothed to prevent inadvertent tissue damage during operative use of the instrument 10 as will hereinafter become apparent.

Similarly, second shank 18 carries, on its end remote from central bend 14, an integral shearing portion 28 which includes a cutting edge 30.

A rivet 32 or other suitable means pivotally connects blade 20 and shearing portion 28 for relative movement of cutting section 22 and cutting edge 30 toward and away from each other along a cutting plane for shearing contact with a surgical suture to be cut. Movement of cutting section 22 and cutting edge 30 relatively toward each other is accomplished by the application of opposed forces to finger bearing surfaces or portions 34, 36 of first and second shanks 16, 18 respectively, these opposed forces being indicated and represented by the reference arrows 38 in FIG. 1. Subsequent return movement of cutting section 22 and cutting edge 30 away from each other is effected by a resilient return urgency imparted by central bend 14 when the surgical user discontinues applying mutually opposed forces 38 to finger bearing surfaces 34, 36.

The strip of material 12 unitarily forming the inventive surgical instrument 10 may advantageously be provided with cutouts of predetermined configuration and at predetermined locations along shanks 16, 18 and central bend 14 to thereby control the resilient properties and characteristics exhibited. In the preferred embodiment herein disclosed, central bend 14 includes an elongated slot 40 defined therein and extending along at least a portion of the arc of bend 14. Slot 40 has the effect of decreasing the magnitude of resilient return urgency imparted to suture remover 10 by the central bend with respect to that spring-type urgency which would otherwise be provided in the absence of such a cutout.

Similarly, one or a plurality of cutouts or apertures 42 may be predeterminately defined in first and second shanks 16, 18—and particularly in finger bearing surfaces 34, 36—to increase their flexibility. As a consequence of these cutouts 42, operative use of the instrument 10 as will hereinafter be described requires increased movement of shanks 16, 18 toward each other on application of opposed forces 38 thereto, thus correspondingly increasing the control provided a user of the instrument 10 in effecting a desired degree of relative movement between blade 20 and shearing portion 28. Those skilled in the art will of course recognize and understand that the precise number and size and configuration of the various cutouts 40, 42 to achieve a desired degree of flexibility and return urgency during operative use of suture remover 10 is at least partly dependent upon the characteristics of the chosen material of construction of resilient strip 12, although the illustrated form of elongated slot 40 in central bend 14 has been determined to be particularly advantageous in appropriately distributing the decrease in return urgency along the desired portion of the length of bend 14. It is, in any event, contemplated that forms of all of the cutouts 40, 42 other than those shown in the drawings might alternatively be employed within the scope and teaching of the invention.

The end of each of first and second shanks 16, 18 remote from central bend 14—at which the shanks are integrally and unitarily attached to blade 20 and shearing portion 28, respectively—incorporates a twist 44 of substantially 90° so as to dispose the blade and shearing portion substantially parallel to each other and generally perpendicular to finger bearing surfaces 34, 36 of first and second shanks 16, 18. Moving next along shanks 16, 18 in the direction of central bend 14, respective contact or abutment shoulders 46, 48 extend from twists 44 and cooperatively interact in the nature of a stop. As the application of opposed finger-induced forces 38 on shanks 16, 18 cause relative movement of the shanks toward each other during operative use of instrument 10, shoulders 46, 48 are correspondingly moved together until—at the end of an operating stroke or suture cutting and gripping closure—the shoulders abuttingly meet or contact. This mutual abutment prevents further pivotal movement of cutting section 22 and cutting edge 30 together along the cutting plane irrespective of the continued application of opposed forces 38 to finger bearing surfaces 34, 36. Consequently, damage to the suture remover 10 due to overclosure or like operative abuse is positively prevented by the mutual abutment of shoulders 46, 48 at the predetermined point constituting the end of the permissible operating stroke of the instrument.

A suture gripping element 50 of generally elongated form integrally depends and is unitarily connected to shearing portion 28 at a bend 52. As perhaps best seen in FIG. 2, gripping element 50—as well as the main body of shearing portion 28—is substantially planar and in the preferred form of instrument 10 gripping element 50 closely overlies a surface area of shearing portion 28 so that they lie in parallel and adjacent planes. It will accordingly be understood that bend 52 bridgingly extends between said adjacently parallel planes to unitarily connect gripping element 50 with shearing portion 28. Put another way, bend 52 displaces gripping element 50 from the plane of shearing portion 28 to an adjacently parallel and overlying position readily apparent in FIG. 2.

The end of suture gripping element 50 remote from its connecting bend 52 is provided with a contact area 54. In the disclosed embodiment shown in the drawings, contact area 54 includes an arcuately convex surface or portion 56 for suture-gripping complimentary mating contact or engagement with the correspondingly concave surface 24 of cutting section 22 during operative use of the instrument 10. In a preferred form of the invention, contact area 54—and more particularly surface 56 thereof—extends beyond cutting edge 30 so that during an operating stroke suture remover 10 initially grips—and then cuts—the suture. An elongated arm 58 extends between contact area 54 and connecting bend 52 of gripping element 50, and is intermediately provided with a narrowed portion 60. This widthwise or transverse narrowing of arm 58 in the area 60 has the effect of distributing operative deformation of gripping element 50 predeterminately along its elongation during use of the instrument 10. More particularly, this resilient deformation of gripping element 50 is caused—as a consequence of the presence of narrowed portion 60—to occur primarily at the narrowed portion rather than at the integral connecting bend 52 where such deformation would otherwise primarily take place and, as a consequence, deterioration in the integrity of connecting bend 52 is minimized and the useful operative life of suture remover 10 correspondingly extended.

Blade 20 is further provided with a protruding dimple or the like extending from its surface adjacently opposing shearing portion 28 for contact with the shearing portion face during a suture cutting and gripping stroke. As cutting section 22 and cutting edge 30 are operatively moved together and dimple 62 on blade 20 slides against the surface of shearing portion 28 rearwardly of rivet 32, the blade and shearing portion are moved slightly apart and, as a consequence, the forward or jaw portions of the blade and shearing portion—and more particularly cutting section 22 and cutting edge 30—are correspondingly urged together into assured suture shearing contact in the cutting plane during their movement toward each other. Dimple 62 additionally decreases friction between blade 20 and shearing portion 28 and thus facilitates operative suture cutting and gripping closure of the instrument 10. It should be clear that dimple 62 could alternatively be provided on the opposed or contact face of shearing portion 28, or the same or similar structures could be defined on both blade 20 and shearing portion 28 for cooperative engagement during an operating stroke of the instrument 10.

Figure 5:
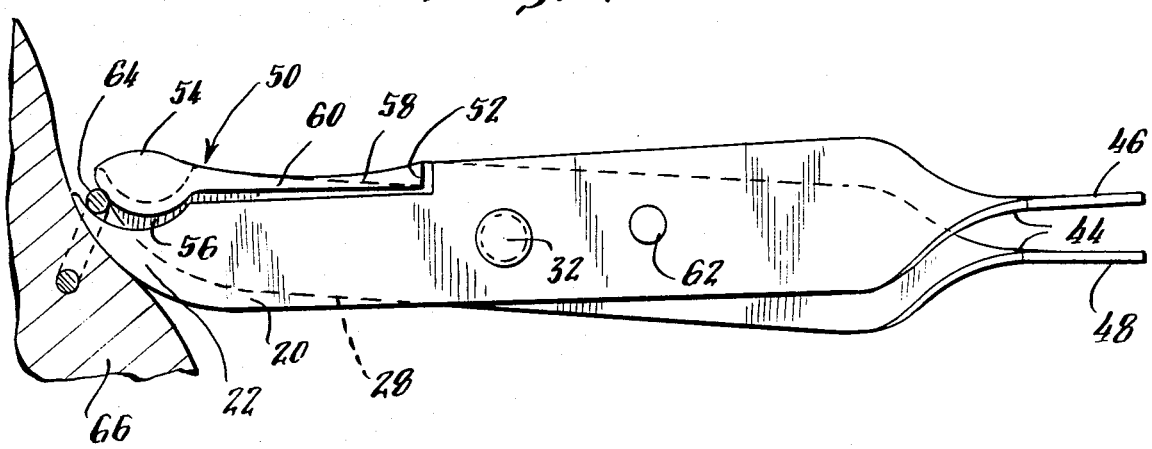
FIG. 5 is a view similar to FIG. 4 in which the operative forward portion of the instrument has been partially closed to grip the suture but prior to cutting thereof.
Figure 6:
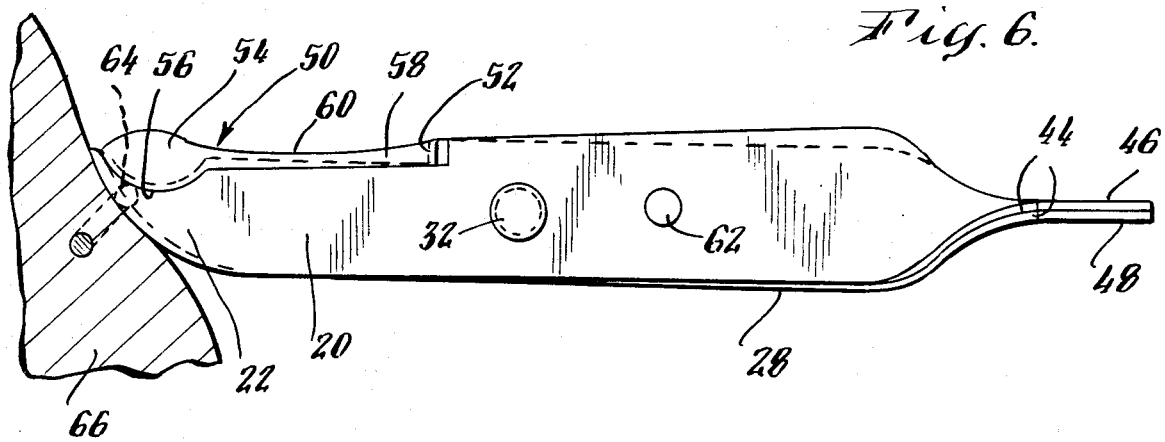
FIG. 6 is a view similar to FIGS. 4 and 5 in which the forward portion of the instrument is shown subsequent to cutting of the suture wherein the jaws of the instrument are fully closed and the suture continues to be gripped to facilitate its withdrawal from the patient's tissue.

In use, and referring now to FIGS. 4 to 6, digging end 26 of blade 20 is inserted between a suture 64 and the tissue 66 in which the suture is tied. Opposed finger-induced forces 38 are applied to the bearing surfaces 34, 36 of shanks 16, 18 to effect an operating stroke or jaw closure of the instrument 10. As cutting section 22 and cutting edge 30 are thereby moved together, suture 64 is initially gripped or held between contact area 54 of gripping arm 50 and cutting section 22 of blade 20—or, more particularly, between complimentary surfaces 24 and 56—prior to actual severing of the suture thread (FIG. 5). Further movement of cutting section 22 and shearing portion 28 together causes cutting edge 30, in cooperation with cutting section 22, to cut suture 64 while the grip of the suture between contact area 54 and cutting section 22 is maintained.

It should be noted that following initial gripping of the suture between contact area 54 and cutting section 22, the further relative movement of cutting section 22 toward cutting edge 30 along the cutting plane for shearing contact with the suture causes contact area 54 of gripping element 50 to be resiliently moved or forced along the cutting plane by reason of its continued contact with cutting section 22. In order to enable such continued movement of contact area 54, gripping element 50 is resiliently deformed substantially perpendicular to its elongation. This deformation is primarily concentrated in the arm 58 of gripping element 50 and, more particularly, at its narrowed portion 60. By so concentrating this resilient deformation at a somewhat central portion of gripping element 58, concentration of these deforming forces at connecting bend 52—which could otherwise severely stress the material at bend 52 causing premature material failure at that point—is prevented, and the useful operative life of the suture remover is notably increased.

The length of the operating stroke or jaw closure of the instrument 10 is limited by the mutual abutment of contact shoulders 46, 48 as seen in FIG. 6. In the absence of such a stroke limiting feature, the continued application of opposed forces 38 to shanks 16, 18 could easily result in the overstressing and consequent material failure of gripping element 50 as deformation thereof continued beyond its ability to resiliently flex.

The present invention accordingly teaches a surgical suture removal instrument advantageously formed of a single piece of material. With the exception of rivet 32, each and every element and structural feature of the disclosed preferred embodiment is inherently unitary and integral with every other element. As a consequence, there are no soldered or welded or other nonintegral connections to fail or at which unusual stresses on the instrument are likely to be concentrated, and the suture remover's reliability is correspondingly increased. Moreover, the relatively small number of requisite manufacturing steps enable this precision instrument to be manufactured at an extremely low production cost. Still further, the various structural features and elements of the one-piece suture remover cooperatively interact with one another to produce an instrument having operating characteristics and abilities beyond the mere sum of its collected parts.

In the embodiment of the invention shown in FIGS. 7-11, the reference numerals applied to like parts shown in FIGS. 1 to 6 are identical to those in FIGS. 7-11, Referring to FIG. 7, the elongated strip 12 fabricated of a flexible and deformable material, such as stainless steel, is provided with a central bend portion 14 having spaced apart, substantially parallel, finger grip parts 16 and 18 respectively. Finger grip 16, at its remote end from the central bend 14, unitarily carries a shank portion 16a, and an integral blade 68 having a cutting surface 70. The blade 68 is also provided with an elongated raised rib 72 located substantially along the longitudinal axis of blade 68. It should be noted that the raised portion 72 is also provided with a corresponding recess 74 on the underside of the blade, as seen in FIGS. 10 and 11. Finger grip 16 also is provided with a twist 44, as well as a contact or abutment shoulder, and a shank portion 18a 46. Blade 68, at its extreme end, is provided with a rounded tip 76.

Shank 18 is disposed substantially parallel to shank 16 and also is provided with a twist 44, as well as contact or abutment shoulder 48, which coacts with the oppositely disposed abutment shoulder 46, to form a stop. At the extreme end thereof is an integral shear blade 78 which is substantially the same configuration as the cutting blade 68, and interacts therewith since the cutting blade is operatively connected to the shear blade by means of a rivet 32. Thus, the rivet, or other suitable means, pivotally connects blade 68 to the shear blade 78. It should be apparent that cutting action of the scissors is achieved by movement of the cutting blade 68 against the shear blade 78 along a cutting plane. This is achieved by applying opposing forces to the resilient finger grip parts 16 and 18 by squeezing the grip parts 16 and 18 together whereby the blade 68 is caused to move relative to the shear blade 78, to thereby effect a cutting action. The blade 78 is provided with an elongated rib 80 substantially similar to the rib 72 on blade 68. A dimple 62 is provided on blade 68 between the pivot point 32 and twist 64, having its projection portion inwardly directed towards said shear blade 78 to slightly separate the blades thereby decrease friction between the blade 68 and the shear blade 78, and thus assist in the cutting action. Moreover, the ribs 72 and 78 serve an important function in that they render the tip 76 of the blades inflexible, and they also bow both the cutting blade 68 and the shear blade 78 so that they overlie each other in parallel planes, and edge to edge contact with a substantially 0° clearance is achieved upon moving the cutting blade and the shear blade into contact with each other. This arrangement reduces the frictional drag, and consequently makes it easier for small children, and people with limited strength to operate the scissors. For example, a small child's fingers which may not be able to manipulate a standard scissors through its finger rings, will be able to squeeze the resilient finger parts of the present one-piece scissors to thereby easily effect a cutting action on a selected material.

The bowed effect on both the cutting blade and the shear blade is clearly illustrated in FIGS. 10 and 11 of the drawings.

While there have been shown and described two embodiments of the present invention, it will be understood that various changes in the form and details of the device illustrated and in its operation may be made by those skilled in the art without departing from the spirit of the invention. It is the intention, therefore, to be limited only as indicated by the scope of the claims appended hereto.

What is claimed is:

1. An improved suture remover, comprising:
    a single elongated strip of resiliently flexible material, said strip being bent substantially midway in its elongation to define a first shank carrying an integral blade at its end remote from said bend and a second shank carrying an integral shearing portion at its end remote from said bend, and said first and second shanks being disposed in substantially spaced apart relation;
    a cutting section on said blade;
    a cutting edge on said shearing portion;
    a twist of substantially 90° in each of said first and second shanks remote from said bend and adjacent said blade and shearing portion so as to dispose said blade and shearing portion in substantially parallel planes;
    means pivotally connecting said blade and shearing portion for movement of said cutting section and cutting edge toward and away from each other along a cutting plane for shearing contact with a suture to be cut, said cutting section and cutting edge being pivotally movable toward each other by selective movement of said first and second shanks toward each other, and being thereafter pivotally moved away from each other by a resilient return urgency imparted by said bend in the strip of material;
    an integral contact shoulder on each of said first and second shanks adjacent said twist for mutual abutment during suture cutting operative use of the suture remover to prevent pivotal movement of said cutting section and cutting edge toward each other beyond a predetermined point and thereby prevent damage to the suture remover; and
    an elongated suture gripping element having a contact area and integrally connected to said shearing portion at an end of said element remote from said contact area, said gripping element being substantially planar along its elongation and including a bend bridging said planar elongation thereof and said integral connection to said shearing portion by which said gripping element is caused to overlay a portion of said shearing portion from which it integrally depends such that relative movement of said cutting edge and cutting section along said cutting plane for shearing contact with the suture during operative use of the suture remover causes deformation of the gripping element as its contact area is resiliently moved along said cutting plane and substantially perpendicular to the elongation of the gripping element.

2. An improved suture remover in accordance with claim 1,
    said cutting section including an arcuately concave portion adjacent its end remote from said pivotal connecting means; and
    said contact area including a correspondingly arcuately convex surface for mating engagement with said concave portion of said cutting section so as to enable a suture to be gripped therebetween as said cutting section and cutting edge are moved toward each other along the cutting plane during operative use of the suture remover.

3. An improved suture remover in accordance with claim 1, further comprising:
    a dimple in at least one of said blade and shearing portion intermediate said pivotal connecting means and said twist and disposed in opposition to the other of said blade and shearing portion for contact therewith during operative use of the suture remover so as to urge said cutting section and cutting edge into assured suture shearing contact during their movement toward each other.

4. An improved suture remover in accordance with claim 1,
    said elongated strip of resiliently flexible material further including at least a cutout of predetermined configuration defined at said bend therein to decrease said resilient return urgency and facilitate ready selective movement of said first and second shanks toward each other during operative use of the suture remover.

5. An improved suture remover in accordance with claim 4,
    said cutout comprising a slot extending along the elongation of said strip of resiliently flexible material.

6. An improved suture remover in accordance with claim 1,
    said gripping element including an elongated arm integrally connecting said contact area and said bend, and said arm having a narrowed portion intermediate its ends for causing said deformation of the gripping element as its contact area is resiliently moved along said cutting plane to occur primarily at said narrowed portion rather than at said integral connection of the gripping element to said shearing portion, thereby minimizing deterioration of said gripping element connection and extending the useful operative life of the suture remover.

7. An improved suture remover in accordance with claim 1,
   each of said first and second shanks having a finger bearing surface upon which respectively opposed finger-urged forces are selectively impartable by a user to cause relative movement of said first and second shanks toward each other during operative use of the suture remover, at least one of said finger bearing surfaces including at least a cutout defined therein for increasing the flexibility of the respective shank and thereby decreasing the force necessary to effect selective relative movement of the shanks toward each other.

8. An improved suture remover in accordance with claim 1,
   at least a portion of said contact area of the gripping element overlaying and extending beyond said cutting edge of the shearing portion so that movement of said cutting section and cutting edge toward each other during suture cutting operative use of the suture remover causes said gripping element to initially grip the suture prior to shearing contact with the suture.

9. A scissors comprising a single elongated strip of resiliently flexible material, said strip being bent substantially midway along its length forming finger gripping sections and first and second shanks which are disposed in a substantially spaced apart relationship, said first shank carrying an integral cutting blade at its end remote from said bend, and said second shank carrying an integral shear blade at its end remote from said bend, a twist of substantially 90° in each of said first and second shanks remote from said bend and adjacent to said cutting blade and shear blade to thereby orient said blades in substantially parallel planes, means pivotally connecting said blades for movement toward and away from each other along a cutting plane for shearing contact with a material to be cut, said cutting blade and shear blade being pivotable movable toward each other by selective movement of said first and second shanks toward each other, an abutment shoulder on each of said first and second shanks adjacent to said twist and extending in a plane substantially perpendicular to the plane of said cutting and shear blades for mutual abutment during the operation of the scissors to prevent pivotal movement of said blades toward each other beyond a predetermined point, said cutting blade and shear blade each having an elongated rib portion which is elevated on the outside of said blade and recessed on the inside of said blade, said rib portions functioning to bow both the cutting blade and shear blade so that edge to edge contact thereof is achieved upon moving said blades toward each other.

10. A scissors as claimed in claim 9 wherein the tips of said blades are rounded and are rendered inflexible by said elongated rib portions.

11. A scissors as claimed in claim 9 further comprising a dimple on one of said blades positioned between said pivotal connection of said blades and said twist, and urging said cutting blade into assured cutting action relative to said shear blade.

12. A scissors as claimed in claim 9 wherein said rib portions each extend along the longitudinal axis of the respective blade and said recesses are positioned in a space confronting manner.

13. A scissors comprising an elongated strip of yieldable and flexible material, said strip being bent substantially midway along its length forming gripping sections and first and second shanks which are disposed in substantially spaced apart relationship, said first shanks having a cutting blade at its end remote from said bend, and said second shank having a shear blade at its end remote from said bend, each of said shanks being twisted in the same direction approximately 90° whereby said cutting blade and shear blade as well as the first and second shanks are oriented in substantially overlying parallel planes which results in maximum opening of the blade tips, means pivotally connecting said blades for movement toward and away from each other along a cutting plane for shearing contact with the material to be cut, said blades being yieldable to urge the same towards each other thereby forming a set with a substantially 0° clearance for effective material cutting, and each of said shanks having a space confronting portion which is in a plane that is substantially perpendicular to the plane of said blades and which forms a stop with the other portion against further movement of said blades when said gripping sections are squeezed toward each other.

14. A scissors as claimed in claim 13 wherein said means pivotally connecting said blades is a rivet.

* * * * *